US00PP27127P3

(12) United States Plant Patent
Van De Pol

(10) Patent No.: US PP27,127 P3
(45) Date of Patent: Sep. 6, 2016

(54) ROSE ROOTSTOCK NAMED 'PROTANO'

(50) Latin Name: *Rosa hybrida*
Varietal Denomination: Protano

(71) Applicant: ROSAFLOR B.V., Leimuiderbrug (NL)

(72) Inventor: Peter A. Van De Pol, Overberg (NL)

(73) Assignee: ROSAFLOR B.V., Leimuiderbrug (NL)

( * ) Notice: Subject to any disclaimer, the term of this patent is extended or adjusted under 35 U.S.C. 154(b) by 126 days.

(21) Appl. No.: 13/998,985

(22) Filed: Dec. 31, 2013

(65) Prior Publication Data

US 2014/0230105 P1 Aug. 14, 2014

(30) Foreign Application Priority Data

May 6, 2013 (QZ) ..... PBR 2013/460

(51) Int. Cl.
*A01H 5/00* (2006.01)
*A01H 5/02* (2006.01)

(52) U.S. Cl.
USPC ..... Plt./101
CPC ..... *A01H 5/0222* (2013.01)

(58) Field of Classification Search
USPC ..... Plt./101
See application file for complete search history.

*Primary Examiner* — June Hwu
(74) *Attorney, Agent, or Firm* — Buchanan, Ingersoll & Rooney PC

(57) ABSTRACT

A new and distinct rose plant is provided which is particularly well suited for service as a rootstock for a rose scion cultivar. More specifically, when so used the scion cultivar exhibits a propensity to yield an increase in biomass and the promotion of faster bud release when compared to the results achieved when the scion cultivar is grown on its own roots or on a standard rootstock, such as 'Natal Briar'. Both higher production rates combined with improved quality in the scion variety are facilitated. The new rose plant displays an upright growth habit with vigorous growth. Small single light pink changing to near white cup-shaped blossoms are formed having five generally heart-shaped petals. Yellow/orange reproductive organs are prominently displayed at the centers of the blossoms. Medium green leaflets with finely serrated margins and a matte upper surface are displayed.

1 Drawing Sheet

Botanical/commercial classification: *Rosa hybrida*/Rose Rootstock.

Varietal denomination: cv. Protano.

SUMMARY OF THE INVENTION

The new variety of *Rosa hybrida* rose rootstock was created by artificial pollination during 2007 at Overberg, The Netherlands, wherein two seedling parents were crossed which previously had been studied in the hope that they would contribute the desired characteristics. The female parent (i.e., the seed parent) was the '04-57' variety (unreleased and non-patented in the United States). The male parent (i.e., the pollen parent) was the '700' variety (unreleased and non-patented in the United States).

The parentage of the new variety can be summarized as follows:

'04-57'×'700'.

The seeds resulting from the above pollination were sown and small plants were obtained which were physically and biologically different from each other. Selective study resulted in the identification of a single plant of the new variety.

It was found that the new rose plant of the present invention:

(a) displays an upright growth habit with vigorous growth,
(b) forms small single light pink changing to near white cup-shaped blossoms having five generally heart-shaped petals with the prominent display of yellow/orange reproductive organs at the center of the blossoms, (c) exhibits medium green leaflets with finely serrated margins having a matte upper surface, and
(d) when used as a rootstock for a rose scion variety exhibits a propensity to induce an increase in biomass and the promotion of faster bud release for the scion variety.

The new variety can be readily distinguished from its '04-57' and '700' parents. More specifically, '04-57' displays flowers that are less flattened when open and possesses more of a Red-Purple tint, and '700' unlike the new variety is sterile and commonly bears more thorns per internode (e.g., 3 thorns per internode).

The new variety provides an advantageous rootstock for use during the production of roses, including cut roses grown under greenhouse growing conditions. When the new variety is utilized as a rootstock, the scion variety commonly grows more rapidly to yield a greater biomass (e.g., 10 percent or more) with thicker and longer stems. Also, a yield of cut flowers commonly takes place earlier than when a standard rootstock, such as 'Natal Briar' (non-patented in the United States) is employed. Both higher production rates and improved quality in the scion variety are made possible. This provides the grower a significant economic advantage. The degree of increase has been found to be influenced by the scion variety in question and the cultivation conditions. Also, the new rootstock may make possible an acceptable yield at lower temperatures and the use of less artificial lighting.

A particularly advantageous increase in biomass has been observed when the scion variety is the 'KORcut 0006' variety (non-patented in the United States), the 'KORsteimm' variety (U.S. Plant Pat. No. 20,700), and the 'KORcoluma' variety (U.S. Plant Pat. No. 17,047). A lesser overall biomass, and lesser stem length, commonly have been found to be exhibited when such scion varieties are grown on their own roots or on a standard 'Natal Briar' rootstock.

Filed concurrently herewith are two additional United States Plant Patent Applications directed to other distinctive new rose rootstocks developed through the plant breeding and selection research of Applicant. These are U.S. Plant patent application Ser. No. 13/998,984 entitled Rose Rootstock Named 'Pronne', and U.S. Plant patent application Ser. No. 13/998,983 entitled Rose Rootstock Named 'Protatu'.

Standard DNA analysis using Simple Sequence Repeat (SSR) or microsatellites can be utilized to distinguish the new 'Protano' cultivar from other rose varieties, including the 'Pronne' and 'Protatu' varieties. The presence or absence of eight standard markers with scored alleles (i.e., RHB303, RHD221, RHE2A, RHI402, RHJ404, RHM405, RHO517, and RHP519) can be utilized and were evaluated with respect to the 'Protano', 'Protatu', and 'Pronne' varieties as reported in the TABLE 1 that follows. This determination was carried out at Stichting Nederlandse Algemene Kwaliteitsdienst Tuinbouw (Netherlands Inspection Service for Horticulture), better known as Naktuinbouw. DNA from leaf samples of each cultivar was extracted using the standard Naktuinbouw CTAB DNA isolation protocol. SSR DNA profiles were generated for each variety. The generated DNA fragments (alleles) were separated by gel electrophoresis. The alleles were scored present or absent and are reported hereafter.

TABLE 1

| | Marker | | | | | | | |
|---|---|---|---|---|---|---|---|---|
| | RHB303 | RHD221 | RHE2A | RHI402 | RHJ404 | RHM405 | RHO517 | RHP519 |
| 'Protano' | G, H | F | D | A, B | D | C, D | C, D | C, F |
| 'Protatu' | H | F | D | A, E | D | B, D | C, D | C, F |
| 'Pronne' | H | F | B, D | A, D | D | C, D | C, D | C |

The difference between 'Protano' and 'Protatu' is 5 of the 53 alleles. The difference between 'Protano' and 'Pronne' is 5 of the 53 alleles The difference between 'Protatu' and 'Pronne' is 6 of the 53 alleles. See G. D. Esselink, M. J. M. Smulders, and B. Voeman, "Identification of cut rose (*Rosa hybrida*) and rootstock varieties using robust sequence tagged microstallite site markers," *Theor Appl Genet*, No. 106, Pages 277 to 286 (2003).

The new variety of the present invention has been found to undergo asexual propagation beginning in 2008 at Overberg, The Netherlands, by the rooting of stem cuttings. Asexual propagation by the above-mentioned technique has shown that the characteristics of the new variety are stable and are strictly transmissible by such asexual propagation from one generation to another. Accordingly, the new variety undergoes asexual propagation in a true-to-type manner.

The new cultivar initially was designated '08-57', and has been named 'Protano'. At times, "PRO-5" has been associated with this cultivar.

BRIEF DESCRIPTION OF THE PHOTOGRAPH

The accompanying photograph shows as nearly true as it is reasonably possible to make the same, in a color illustration of this character, a typical specimen of a plant of the new variety. The rose plant of the new variety was approximately five years of age and was observed during June while growing outdoors on its own roots in sandy soil at Overberg, The Netherlands. Floral buds and blossoms in various stages of development as well as medium green foliage with serrated margins are depicted. The very light pink blooms tend to fade to near white with full maturity.

DETAILED BOTANICAL DESCRIPTION

The chart used in the identification of the colors is that of The Royal Horticultural Society (R.H.S. Colour Chart-1995 edition or equivalent). The description is based on the observation of five-year-old plants during June while growing outside in sandy soil at Overberg, The Netherlands.

Class: Most closely resembles *Rosa multiflora.*

Plant:

*Growth habit*.—Substantially upright.

*Height*.—Commonly approximately 1.75 m on average.

*Width*.—Commonly approximately 60 cm on average.

*Roots*.—Exhibit no propensity to sucker when used as a rootstock, display good compatibility with scions, provide good anchorage, and impart good vigor when used as a rootstock.

Branches:

*Stems*.—Color: commonly near Yellow-Green Group 144B with anthocyanin coloration at the tips of young branches.

*Diameter*.—Commonly approximately 7 mm on average.

*Texture*.—Generally smooth.

*Internode length*.—Commonly approximately 7 cm on average. Such internode length renders the plant well suited for stenting as indicated hereafter.

*Thorns*.—Commonly absent or present in a low frequency of approximately 1 per internode, approximately 8 mm in length on average, and of varied coloration on young thorns ranging from near Orange-Red Group N34A to Yellow-Green Group 145A, and commonly near Greyed-Purple Group 187A on mature thorns.

Foliage:

*Petioles*.—Length: approximately 17 mm on average. Diameter: approximately 1 mm on average. Texture: commonly slightly glandular. Color: commonly near Red Group 53B on the upper side and near Yellow-Green Group 144C on the underside.

*Rachis*.—Color: commonly near Yellow-Green Group 146B on both surfaces.

*Leaves*.—Length: commonly approximately 9 cm on average. Width: commonly approximately 6 cm on average.

*Leaflets*.—Number: commonly 7 and 9. Shape: generally elliptical with a somewhat acuminate tip and an obtuse base. Size: the terminal leaflets commonly are approximately 70 mm in length on average, and approximately 34 mm in width on average. Serration:

small and fine and commonly approximately 1 mm in size. Texture: with a matte upper surface. Commonly near Yellow-Green Group 146C on both surfaces and without anthocyanin coloration.

Inflorescence:

*Number of flowers*.—Commonly borne in clusters.

*Type*.—Single.

*Peduncle*.—Length: commonly approximately 1.5 cm on average. Diameter: commonly approximately 0.8 mm on average. Texture: commonly very glandular. Color: commonly near Yellow-Green Group 143C.

*Pedicel*.—Color: commonly near Yellow-Green Group 143C with weak anthocyanin coloration solely on the upper side.

*Buds*.—Shape: substantially conical. Color: commonly near Greyed-Purple Group 187C with weak anthocyanin coloration solely on the upper side.

*Flower*.—Shape: cup-shaped, and substantially flattened. Diameter: small, approximately 4 cm on average. Number: commonly approximately 80 to 120 per inflorescence on average. Color (in the course of opening): Upper surface: light pink, near White Group 155A commonly with a tint of near Red-Purple Group 62B. Under surface: light pink, near White Group 155A commonly with a tint of near Red-Purple Group 62B. Color (mature open flower): Upper side: near White Group NN155D. Under side: near White Group NN155D. Fragrance: none detected. Petal number: 5 under normal growing conditions. Petal shape: generally heart-shaped. Petal arrangement: slightly imbricated, and without petaloids. Stamen number: approximately 80 on average. Filaments: near Yellow Group 2B in coloration. Anthers: regularly arranged around the styles, and commonly near Yellow Group 14C in coloration. Pollen: present, and near orange/yellow in coloration. Pistils: connated and fused. Stigmas: commonly near Yellow-Green Group 154A in coloration. Styles: commonly near Yellow-Green Group 145A in coloration. Lastingness: commonly approximately 15 days on the plant and influenced by environmental conditions.

*Sepals*.—Length: commonly approximately 1 to 1.5 cm on average. Width: commonly approximately 2 to 3 mm on average. Color: with some anthocyanin coloration when buds are closed. Texture: slightly rough with the presence of glands.

*Hips*.—Shape: generally oval. Size: commonly approximately 9 mm in length on average, and approximately 8 mm in diameter on average. Color: near Red Group 45A.

Development:

*Vegetation*.—Very strong.

*Blooming*.—Commonly commences and ends in June.

*Hardiness*.—Has well withstood −15° C. at Overberg, The Netherlands.

*Tolerance to diseases*.—Good, with no particular susceptibility to common diseases having been encountered during observations to date.

*Asexual reproduction*.—Cuttings readily undergo rooting.

*Use as understock*.—Stenting can be utilized when the new variety serves as a rose understock for a scion rose variety. In this instance, quick overall propagation can be achieved by grafting the scion variety on an unrooted cutting of the new variety. A resulting complete plant can be formed thereafter in approximately three weeks. This technique was developed by Peter A. van de Pol of Wageningen Agricultural University (The Netherlands). The word "stenting" is a contraction of the Dutch words "Stekken" (rooting of a cutting) and "Enten" (grafting). The technique and word were first published in 1979 in the Dutch *Vakblad voor de Bloemisterij*, No. 26, Pages 40 to 41, and in English in 1982, "Stenting of roses; A method for quick propagation by simultaneously cutting and grafting," *Scientia Horticulture*, No. 17, Pages 187 to 196.

The new 'Protano' variety has not been observed under all possible environmental conditions to date. Accordingly, it is possible that the phenotypic expression may vary somewhat with changes in light intensity and duration, cultural practices, and other environmental conditions.

I claim:

1. A new and distinct rose plant characterized by the following characteristics:

(a) displays an upright growth habit with vigorous growth, (b) forms small single light pink changing to near white cup-shaped blossoms having five generally heart-shaped petals with the prominent display of yellow/orange reproductive organs at the center of the blossoms, (c) exhibits medium green leaflets with finely serrated margins having a matte upper surface, and (d) when used as a rootstock for a cut rose scion variety exhibits a propensity to yield an increase in biomass and the promotion of faster bud release for the scion variety;

substantially as shown and described.

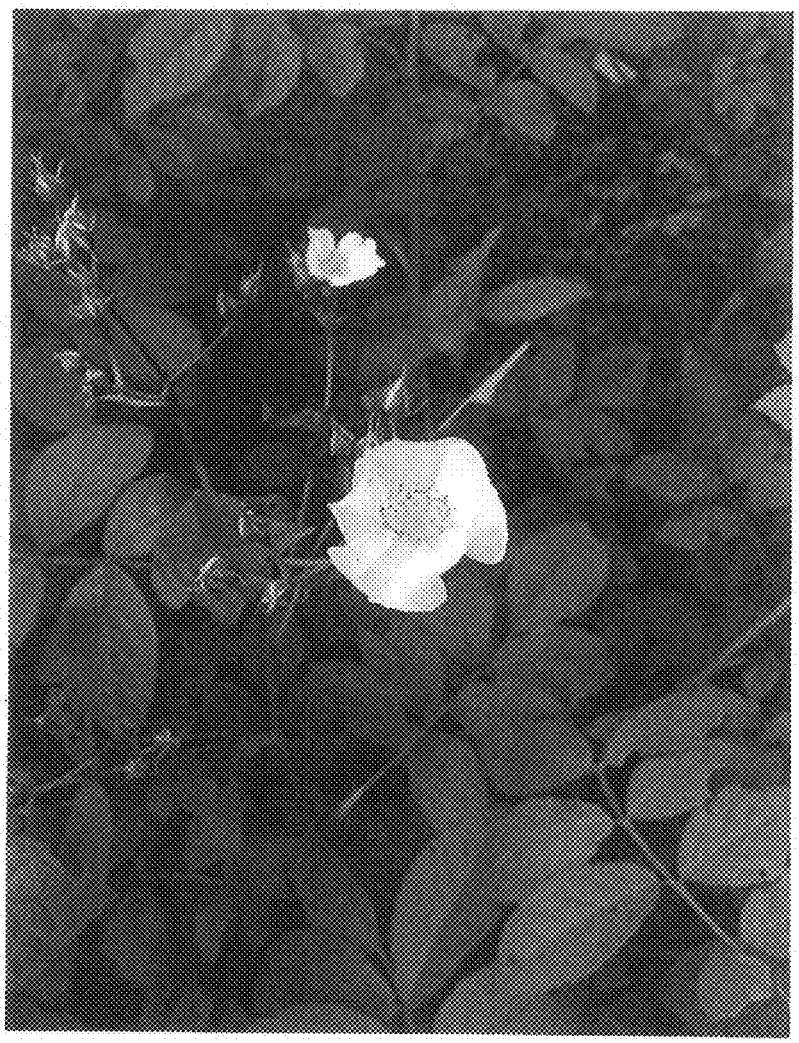

* * * * *